United States Patent [19]

Depel et al.

[11] Patent Number: 4,582,058

[45] Date of Patent: Apr. 15, 1986

[54] TRACHEOSTOMA VALVES

[75] Inventors: William A. Depel, Lowell; Bernd Weinberg; Jerald B. Moon, both of West Lafayette, all of Ind.

[73] Assignees: Bivona, Inc., Gary; Purdue Research Foundation, West Lafayette, both of Ind.

[21] Appl. No.: 674,552

[22] Filed: Nov. 26, 1984

[51] Int. Cl.$^4$ ............................................. A61M 5/00
[52] U.S. Cl. ........................... 128/207.17; 128/207.16; 137/512.3; 623/9
[58] Field of Search ...................... 128/207.17, 207.14, 128/207.16, 203.11, 203.13; 3/1.3; 137/512.3, 863

[56] References Cited

U.S. PATENT DOCUMENTS

| | | | |
|---|---|---|---|
| 2,339,048 | 1/1944 | Bixler | 137/512.3 |
| 3,228,409 | 1/1966 | Godel | 137/512.3 |
| 3,342,200 | 9/1967 | Wilcox | 137/512.3 |
| 3,683,931 | 8/1972 | Chelucci et al. | 128/207.16 |
| 3,692,071 | 9/1972 | Begleiter | 137/512.3 |
| 4,106,502 | 8/1978 | Wilson | 128/203.11 |
| 4,325,366 | 4/1982 | Tabor | 128/207.16 |
| 4,494,252 | 1/1985 | Chaoui | 128/207.17 |

Primary Examiner—Stephen C. Pellegrino
Assistant Examiner—Mark Rooney
Attorney, Agent, or Firm—Emrich & Dithmar

[57] ABSTRACT

A tracheostoma valve assembly for use with a tracheostomy tube or a speech prosthesis device includes a tubular housing structure containing a spring biased main valve which, during normal vegetative breathing, will remain open, and which, during normal air flow associated with speech, will close. The valve assembly includes a separate external relief valve which is closed during normal vegetative breathing and speaking and which opens to release the increased air pressure within the tubular housing resulting from a substantially increased air pressure within the valve assembly and automatically closes when the air pressure is reduced in the valve assembly.

20 Claims, 15 Drawing Figures

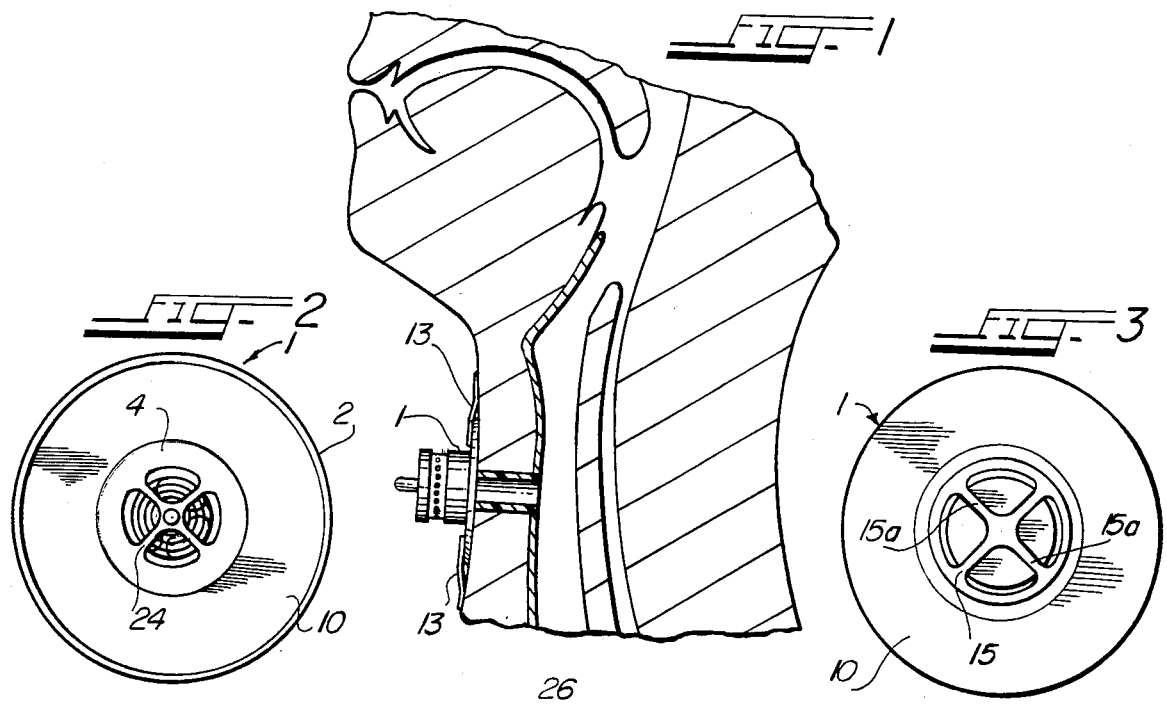
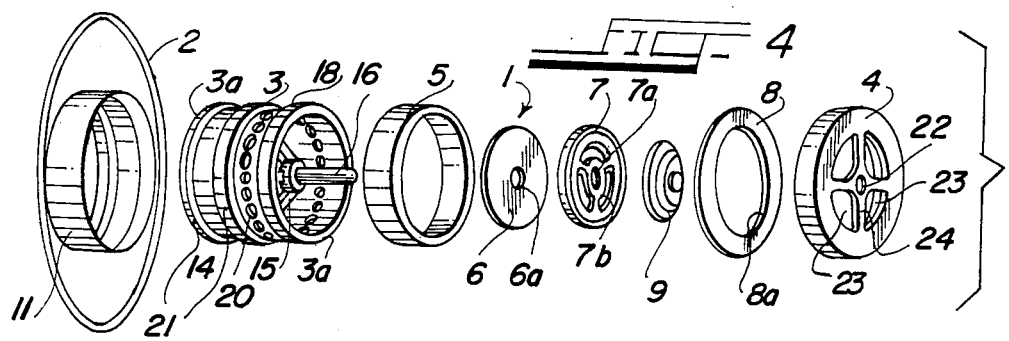
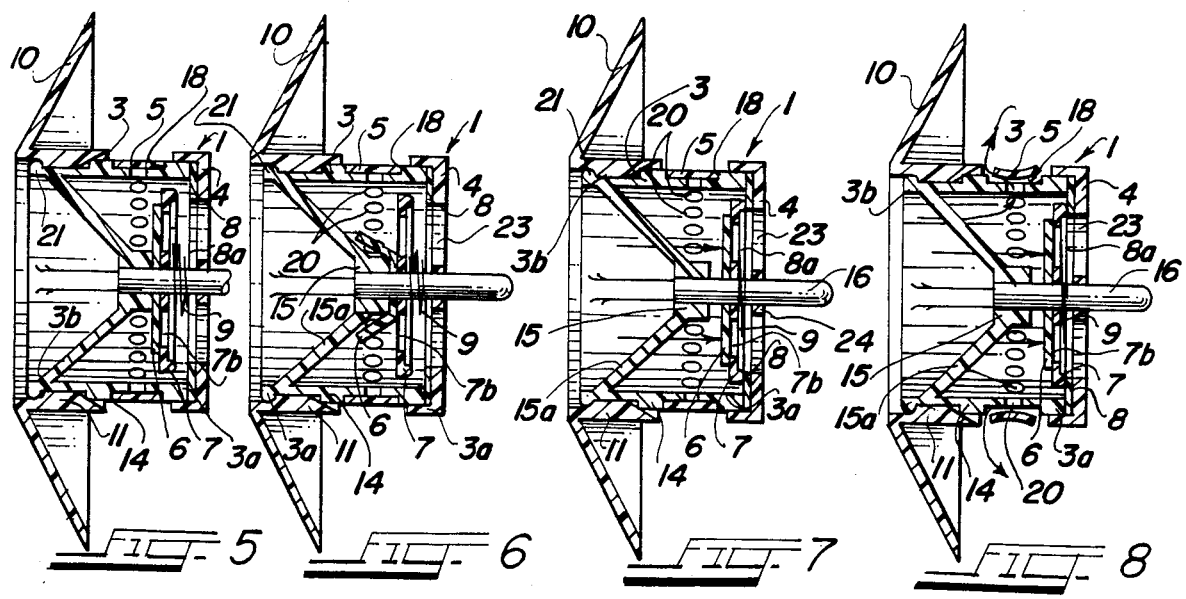

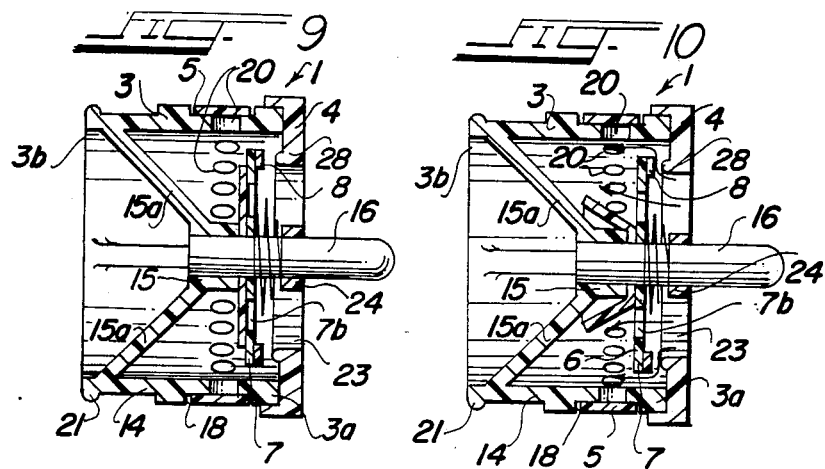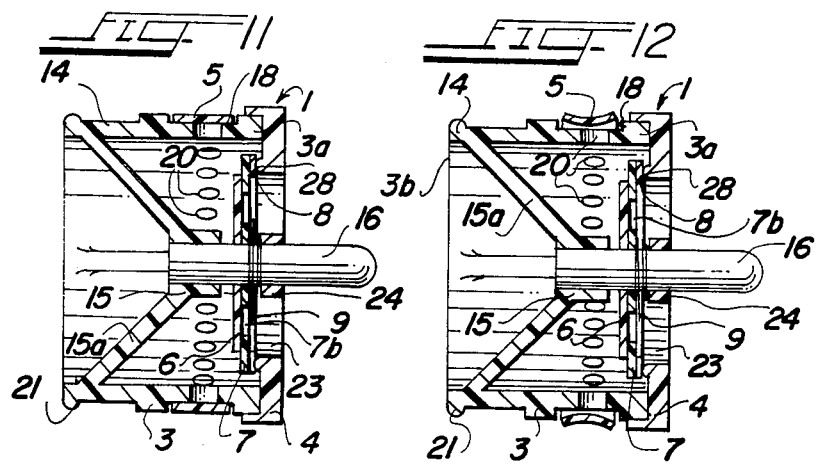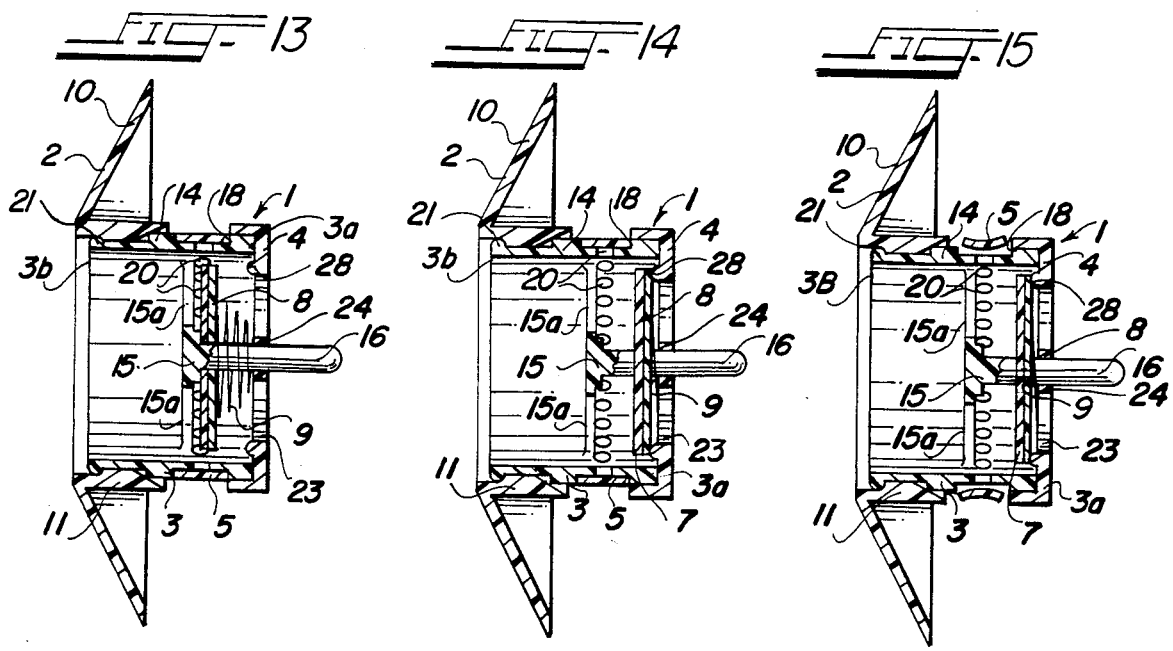

TRACHEOSTOMA VALVES

BACKGROUND OF THE INVENTION

The present invention relates to tracheostoma valves. Tracheostoma valves are currently used in conjunction with speech prosthesis devices and with speaking or fenestrated tracheostomy tubes as a means of diverting exhaled air which would otherwise pass through the tracheostoma to enable the user to speak. It is envisioned the valves may be used as rehabilitation devices for patients seeking to refine esophageal speech and as part of other surgical prosthetic forms of speech rehabilitation.

It is a primary object of the present invention to provide a novel tracheostoma valve.

Another object of the present invention is to provide a novel tracheostoma valve of the disc-valve type which is constituted and arranged in a novel and expeditious manner.

Tracheostoma valves having a flexible valve diaphragm have been heretofore known in the art being shown, for example, in U.S. Pat. No. 4,325,366, issued Apr. 20, 1982 to Carl J. Tabor, and in an application for U.S. Pat., Ser. No. 316,055, filed Oct. 29, 1981, by Eric D. Blom and Mark I. Singer. However, such prior art valve structures possess several inherent disadvantages, such as, for example, experiencing difficulties in remaining open to accommodate a wide range of pressure and flow conditions associated with breathing and physical exercising, and having flexible valving diaphragm members which are extremely difficult to produce in mass production with desired precision. Also, such flexible valve diaphragms include a crease therein when in the open position, which crease does not provide an adequate seal when the diaphragm is then positioned in the closed position. Also, such valve structures readily fatigue in that they change over time and do not retain uniform physical properties during usage, such as, for example, such valve structures become more flexible through usage and thier position at rest varies.

An important object of the present invention is to overcome the difficulties of heretofore known tracheostoma valves in a novel and expeditious manner.

Another object of the present invention is to provide a novel tracheostoma valve which accommodates normal vegetative breathing during various physical activities, during speaking and during coughing in a novel and expeditious manner.

A further object of the present invention is to provide a novel tracheostoma valve which has improved sealing characteristics in the closed or speaking position.

Another object of the present invention is to provide a novel tracheostoma valve the operating characteristics of which may be readily varied to meet the needs of both the same individual and different individuals using the valve and which permits air volumes and/or airflows to enter the valve and the lungs unobstructed when in the open or inhaling position.

Yet another object of the present invention is to provide a novel tracheostoma valve which may be readily disassembled and assembled for purposes of cleaning, repairing, and the like.

A further object of the present invention is to afford a novel tracheostoma valve of the aforementioned type which is practical, efficient and reliable in operation and which may be readily and economically produced commercially.

Other and further objects of the present invention will be apparent from the following description and claims and are illustrated in the accompanying drawings which, by way of illustration, show the preferred embodiment of the present invention and the principles thereof and what we now consider to be the best mode in which we have contemplated applying these principles. Other embodiments of the invention embodying the same or equivalent principles may be used and changes may be made as desired by those skilled in the art without departing from the present invention and the purview of the appended claims.

DESCRIPTION OF THE DRAWINGS

In the drawings:

FIG. 1 is an elevational view of a tracheostoma valve embodying the principles of the present invention, showing a tracheostoma valve affixed to the skin around a tracheostoma;

FIG. 2 is a front-end elevational view of the tracheostoma valve shown in FIG. 1;

FIG. 3 is a rear end elevational view of the tracheostoma valve shown in FIG. 1;

FIG. 4 is an exploded perspective view of the tracheostoma valve shown in FIG. 1;

FIG. 5 is a longitudinal sectional view through the tracheostoma valve shown in FIG. 1, showing the tracheostoma valve in the neutral position;

FIG. 6 is a longitudinal sectional view through the tracheostoma valve shown in FIG. 1, showing the tracheostoma valve in the fully open position; and FIG. 7 is a longitudinal sectional view through the tracheostoma valve shown in FIG. 1, showing the tracheostoma valve in the fully closed position;

FIG. 8 is a longitudinal sectional view through the tracheostoma valve shown in FIG. 1, showing the valve in "blow-out" position such as, for example, when the person wearing the same coughs, or the like;

FIG. 9 is a longitudinal sectional view through a further embodiment of the tracheostoma in accordance with the present invention, showing the tracheostoma valve in the neutral position;

FIG. 10 is a longitudinal sectional view through the tracheostoma valve shown in FIG. 9, showing the tracheostoma valve in the fully open position; and FIG. 11 is a longitudinal sectional view through the tracheostoma valve shown in FIG. 9, showing the tracheostoma valve in the fully closed position;

FIG. 12 is a longitudinal sectional view through the tracheostoma valve shown in FIG. 9, showing the tracheostoma valve in "blow-out" position such as, for example, when the person wearing the same coughs, or the like;

FIG. 13 is a longitudinal sectional view through still another embodiment of the tracheostoma valve in accordance with the present invention, showing the tracheostoma valve in the fully open position;

FIG. 14 is a longitudinal sectional view through the tracheostoma valve shown in FIG. 3 showing the valve in the fully closed position; and FIG. 15 is a longitudinal sectional view through the tracheostoma valve shown in FIG. 13, showing the valve in "blow-out" position such as, for example, when the person wearing the same coughs, or the like.

DETAILED DESCRIPTION OF THE INVENTION

A tracheostoma valve assembly 1, as shown in FIGS. 1-8, illustrates one preferred embodiment of the present invention. The tracheostoma valve assembly 1 includes an annular base member 2 mounted on one end portion 3b of a cylindrical-shaped central body portion or sleeve 3, a cover or end cap 4 mounted on the other end portion 3a of the sleeve 3, a dual valve structure which includes an external blow-out or relief valve means, consisting of a band ring 5 mounted around the central portion of the sleeve 3, and an internal valve means consisting of a flexible silicone valve member 6, a valve disc 7, a sealing ring 8 and spiral spring 9 mounted in the end portion of the sleeve 3 which is adjacent to the end cover 4, FIGS. 5-8, as will hereinafter be discussed.

The base 2, the band ring 5, the valve member 6 and the sealing ring 8 are, preferably comprised of a soft, resilient material, such as, for example, silicone; and the sleeve 3, cover 4 and valve disc 7 preferably are made of a suitable hard, light weight plastic material, and the spring 9 is preferably made of a suitable corrosion-resistant material, such as, for example, stainless steel or spring steel.

The base 2 is preferably of a one-piece molded construction and embodies an annular flange 10 thereon projecting radially outwardly from one end of a tubular body portion or collar 11 (FIGS. 4-8). The flange 10 is resilient and flexible so that it is free to move between the position shown in FIGS. 5-8, wherein it extends in somewhat over-lying position relative to the collar 11, and a relatively flat position, as shown in FIG. 1, to which it is moved when the valve assembly 1 is disposed in operative position on a person wearing the same. The flange 10 may be secured to the person wearing the valve assembly 1 by any suitable means, such as, for example, an adhesive on the face thereof remote from the collar 11, or as shown in FIG. 1, by an annular tape 13, secured to the person and to the flange 10 in over-lying relation to the annular outer edge of the base 2.

The sleeve 3 is, preferably, of a one-piece construction and embodies a tubular housing 14 having a spider 15 disposed therein, FIGS. 3-8, the spider 15 having a post 16 projecting outwardly therefrom through one end 3a of the sleeve 3 along the longitudinal center line of the latter, FIGS. 4-8, and depending legs 15a which extend forwardly to engage the walls of the sleeve 3. The housing 14 of the sleeve 3 has an annular groove 18 formed in and extending around the outer surface thereof, with preferably, a plurality of holes or openings 20 extending through the wall of the housing 14, within the annular groove 18, the opening or openings 20 being disposed radially in the wall with respect to the spider 15 in surrounding relation to the post 16, FIGS. 5-8. In the assembled valve assembly 1, the band ring 5 is mounted in the annular groove 18 in snug fitting, overlying relation to the opening or openings 20 to complete the external blow-out or relief valve means, which will be discussed in greater detail presently.

When the valve assembly 1 is completed, the base 2 is mounted on the end portion 3b of the sleeve 3 remote from the post 16 with a snug, but freely removable fit. Preferably, the sleeve 3 has a flange 21 on the end 3b adjacent to the base 2 on the sleeve 3. At the other end 3a of the sleeve 3, the cover 4 is mounted on the sleeve 3 with a snug, but freely removable fit, in outwardly spaced relation to the band ring 5, FIGS. 5-8. The cover 4 is in the form of a spider 24, FIG. 4, which has an opening 22 through the center thereof, through which the post 16 extends in the valve assembly 1 and a plurality of openings 23 therein which permits air to be inhaled into the valve assembly 1, as will hereinafter be described.

The internal valve means of the valve assembly 1 is comprised of a flexible silicone valve member 6, having a central opening 6a therein adapted to have the post 16 inserted therethrough, positioned adjacent a valve disc 7 having a central opening 7a therein and adapted to have the post 16 inserted therethrough. The valve member 6 is smaller in diameter then the valve disc 7. The disc 7 has a plurality of openings 7b therein (three are shown in FIG. 4), which openings 7b cooperate with the valve member 6 during the inhalation, and a central opening 7a therein adapted to have the post 16 inserted therethrough. However, it is within the scope of the present invention to design a disc 7 having a single arcuate shaped opening therein which cooperates with the valve member 6. The valve member 6 is smaller in diameter then the valve disc 7. The disc 7 and openings 7b (FIG. 4) cooperate with the flexible valve member 6 during the inhalation mode or position (FIG. 6) to provide, in effect, a first valve means within the internal valve means and to permit relatively unobstructed breathing through the openings 7b and past the flexible valve member 6, the position as shown in FIG. 6 and depicted by the arrows therein.

A second valve means within the internal valve means is comprised of the valve disc 7, which is smaller in diameter than the sleeve 3, and which has a central opening 7a therein, FIG. 4. When the valve assembly 1 is completed, the disc 7 is mounted on the post 16 with a snug, but freely slidable fit, the post 16 extending through the opening 7a. Preferably, the disc 7 cooperates with a washer or sealing ring 8, made of a suitable soft, resilient material, such as, for example, silicone, associated therewith, the sealing ring 8 having an enlarged opening 8a through the central portion thereof and being mounted onto the end 3a of the sleeve 3 and retained in place by the end cover 4. The disc 7 cooperates with the sealing ring 8 when the person is in the speaking mode or position to fully close and seal the internal valve means of the valve assembly, the position as shown in FIG. 7.

The spiral spring 9 is mounted on the post 16 in surrounding relation thereto, between the sealing ring 8 and the central portion of the spider 24 of the cover 4. The spring 8 engages the disc 7 to predeterminely position and bias the disc 7 away from the sealing ring 8 to permit normal exhalation and breathing to occur, the position of the valve assembly as shown in FIG. 5.

In the operation of the valve assembly 1, during normal exhalation, as shown in FIG. 5, the spring 9 is effective to hold the disc 7 against, or closely adjacent to the spider 15 in the housing 3 and against the flexible valve member 6. In this position, air may freely flow around the disc 7 and out of the valve assembly 1. When a person wearing the valve assembly inhales, the air passes through the openings 7b and moves the flexible valve member 6 from the closed position (FIG. 5) to the open position (FIG. 6), thus operatively moving both the first valve means and the second valve means of the internal valve structure from the closed position to the open position. When a person wearing the valve assembly 1 wishes to speak, the person's increased respiratory effort, for example, airflow, pressure or the like, from the lungs or trachea 26 is effective to move the flexible valve member 6 against the valve disc openings 7b to close the same and to move the disc 7 away from the spider 15, against the urging of the spring 9 and into position to press the disc 7 into sealing engagement with the sealing ring 8, the position as shown in FIG. 6. Thus, sealed, the tracheostoma valve directs the exhaled air through a fenestrated tube or a tracheoesophageal puncture voice prosthesis device enabling speech. When the person stops speaking, the attendent increased air pressure within valve assembly 1 decreases, the spring 9 is again effective to move the disc 7 back toward the spider 15, out of sealing engagement with the sealing ring 8 and thereby permit the exhalation and flow of air through the valve assembly 1 to resume, the position as shown in FIG. 5. However, when large pressures are generated within the valve assembly 1, such as, for example, when a person wearing the same coughs, or the like, this buildup of air pressure is effective to move the flexible valve member 6 against the openings 7b in the valve disc 7 and to move the disc 7 against the urging of the spring 9 into sealing engagement with the sealing ring 8. Under such circumstances, if the closing of the disc 7 against the sealing ring 8 were permitted to continue to prevent the flow of air outwardly from the trachea 26 of the person wearing the valve 1, the person would be in distress. However, with the novel valve assembly 1, when a large air pressure buildup occurs, thus closing the disc 7 against the sealing ring 8, the increased air pressure is effective to cause the elastic band ring 5 to be displaced outwardly away from the sleeve 3, the position as shown in FIG. 7. The air pressure exerted outwardly (shown by arrows in FIG. 7) through the opening or openings 20 is effective to displace the ring 5 and permit the air to flow outwardly through the opening or openings 20 past the band ring 5. Accordingly, the present invention provides a separate external blow-out or relief valve means which may be predeterminely tuned and sized to open and release the increased air pressure within the valve assembly, and which automatically closes to restore itself when the air pressure within the assembly is reduced therein, a result which has been heretofore been unattainable by the prior art structures.

Thus, the valve assembly 1 effectively accommodates breathing during various types of activities, ranging from exercise to normal vegetative breathing, speaking, and coughing and permits the control of the sensitivity of the external blow-out valve means by varying the dimensions of the opening or openings 20 and the modulous of the band ring 5 and the internal valve means with respect to each other to provide a valve assembly wherein the closing resistance is precisely controlled by the predetermined spring resistance, and the dimensions of the disc or sleeve, a result that permits the accommodation of unlimited breathing requirements of various individuals.

A further embodiment of the tracheostoma valve assembly 1 in accordance with the present invention is shown in FIGS. 9–12, and like numerals have been used throughout the several views to designate the same or similar parts of the first embodiment of FIGS. 4–8. Although the tracheostoma valve assembly 1 of this embodiment includes an annular base member 2 mounted on one end portion 3b of a cylindrical-shaped central body portion or sleeve 3, a cover or end cap 4 mounted on the other end portion 3a of the sleeve and a dual valve structure, as shown in FIGS. 5–8, the dual valve structure has been modified in that the internal valve means includes a flexible silicone valve member 6, a valve disc 7, a sealing ring 8 mounted to the valve disc 7 and spiral spring 9 mounted in the end portion of the sleeve 3 which is adjacent to the end cover 4, FIG. 9–12, as will hereinafter be discussed.

The sleeve 3 is, preferably, of a one-piece construction and embodies a tubular housing 14 having a spider 15 disposed therein, FIGS. 9–12, the spider 15 having a post 16 projecting outwardly therefrom through one end 3a of the sleeve 3 along the longitudinal center line of the latter, FIGS. 9–12. The housing 14 of the sleeve 3 has an annular groove 18 formed in and extending around the outer surface thereof, with a plurality of holes or openings 20 extending radially through the wall of the housing 14, within the annular groove 18, the openings 20 being disposed and positioned in the sleeve between where the angled depending legs 15a engage the walls of the sleeve 3 and the spider 15 in surrounding relation to the post 16, FIGS. 9–12. In the assembled valve assembly 1, the band ring 5 is mounted in the annular groove 18 in snug fitting, overlying relation to the opening or openings 20 to complete the external blow-out valve means.

When the valve assembly 1 is completed, the base 2 is mounted on the end portion of the sleeve 3 remote from the post 16 with a snug, but freely removable fit. Preferably, the sleeve 3 has a flange 21 on the end 36 adjacent to the base 2 on the sleeve 3. At the other end 3a of the sleeve 3, the cover 4 is mounted on the sleeve 3 with a snug, but freely removable fit, in outwardly spaced relation to the band ring 5, FIGS. 9–12. The outer end of the cover 4 is in the form of a spider 24, FIG. 4, which has an opening 22 through the center thereof, through which the post 16 extends in the completed valve assembly 1. A plurality of openings 23 is provided in the cover 4 which permit air to be inhaled into the valve assembly 1, as will hereinafter be described. Additionally, the cover 4 includes an annular valve seat 28 embodied therein in surrounding relation to the cover spider 24. The valve seat 28 is smaller in diameter than the disc 7 and cooperates with sealing ring 8 mounted on the disc 7 to provide sealing engagement of the internal valve means when in the speaking mode or position (FIG. 11) or the blow-out mode or position (FIG. 12), as will hereinafter be described.

The internal valve means of the valve assembly 1 is comprised of a flexible silicone valve member 6, having a central opening 6a therein adapted to have the post 16 inserted therethrough, positioned adjacent a valve disc 7 having a central opening 7a therein and adapted to have the post 16 inserted therethrough. The valve member 6 is smaller in diameter then the valve disc 7. The disc 7 has a plurality of openings 7b therein (FIG. 4), which openings 7b cooperate with the flexible valve member 6 during the inhalation position (FIG. 10) to provide in effect a first valve means within the internal valve means and to permit relatively unobstructed breathing through the openings 7b and past the flexible valve member 6, the position as shown in FIG. 10 and depicted by the arrows therein.

A second valve means within the internal valve means is comprised of the valve disc 7, which is smaller in diameter than the sleeve 3, and which has a central opening 7a therein, FIG. 4. The valve disc 7 and sealing ring 8 mounted thereon cooperate with the annular valve seat 28 of cover 4. When the valve assembly 1 is assembled, the disc 7 and sealing ring 8 thereon, is mounted on the post 16 with a snug, but freely slidable fit, the post 16 extending through the opening 7a. The disc 7 and sealing ring 8 cooperate with the annular valve seat 28 when the person is in the speaking mode or position to fully close and seal the internal valve means of the valve assembly, the position as shown in FIG. 11.

The spiral spring 9 is mounted on the post 16 in surrounding relation thereto, between the disc 7 and the central portion of the spider 24 in the cover 4. The spring 8 engages the disc 7 to predeterminely bias the disc 7 and sealing ring 8 thereon away from the annular valve seat 28 to permit normal exhalation and breathing inhalation to occur, the position of the valve assembly, as shown in FIGS. 9 and 10.

In the operation of the valve assembly 1, during normal exhalation, as shown in FIG. 9, the spring 9 is effective to bias the disc 7 against, or closely adjacent to the spider 15 in the housing 3 and against the flexible valve member 6. In this position, air may freely flow around the disc 7 and out of the valve assembly 1 during normal exhaling. When a person wearing the valve assembly inhales, the air passes through the openings 7b and moves the flexible valve member 6 from the closed position (FIG. 5) to the open position (FIG. 6), thus operatively moving the first valve means of the internal valve structure from a closed position to an open position. When a person wearing the valve assembly 1 wishes to speak, the person's increased respiratory effort, for example, airflow, pressure or the like, from the person's lungs or trachea 26 is effective to move the flexible valve member 6 against the valve disc openings 7b to close the same and to move the disc 7 away from the spider 15, against the urging of the spring 9 and into position to press the disc 7 and sealing ring 8 thereon into sealing engagement with the annular valve seat 28, the position as shown in FIG. 11. Upon sealing, the valve assembly diverts the exhaled air through a fenestrated tube or a tracheoesophageal puncture voice prosthesis device enabling speech. When the person stops speaking, and, this increased air pressure within the valve assembly 1 decreases, the spring 9 is again effective to move the disc 7 back toward the spider 15, out of sealing engagement with the annular valve seat 28 and thereby permit a normal flow of air through the valve assembly 1 to resume, the position as shown in FIG. 9. However, when large pressures are generated within the valve assembly 1, such as, for example, when a person wearing the same coughs, or the like, this buildup of air pressure is effective to move the flexible valve member 6 against the openings 7b in the valve disc 7 and to move the disc 7 against the urging of the spring 9 into sealing engagement with the annular valve seat 28. Under such circumstances, if the closing of the disc 7 against the valve seat 28 were permitted to continue to prevent the flow of air outwardly from the trachea 26 of the person wearing the valve 1, the person wearing the same would be in distress. However, with the novel valve assembly 1, when a large air pressure buildup occurs, thus closing the disc 7 against the annular valve seat 28, the increased air pressure is effective to cause the elastic band ring 5 to be displaced outwardly away from the sleeve 3, the position as shown in FIG. 12, with the air pressure exerted outwardly (shown by arrows) through the openings 20 being effective to so displace the ring 5, and permit the air to flow outwardly through the opening or openings 20 past the band ring 5 and to provide the separate external blow-out or relief valve means in accordance with the present invention, which relief valve means automatically closes to restore itself when the air pressure within the assembly is reduced therein.

A further embodiment of the tracheostoma valve assembly 1, in accordance with the present invention, is shown in FIGS. 13–15. In this embodiment, the tracheostoma valve assembly 1 includes, as set forth above, an annular base member 2 mounted on one end portion of a cylindrical-shaped central body portion or sleeve 3, a cover or end cap 4 mounted on the other end portion of the sleeve 3 and a dual valve structure. The dual valve structure includes a separate external blow-out valve means, consisting of a band ring 5 mounted around the central portion of the sleeve 3, and an internal valve means consisting of a valve disc 7, a sealing ring 8 and mounted on the disc a spiral spring 9 mounted in the end portion of the sleeve 3 which is adjacent to the end cover 4, FIGS. 13–15, as will hereinafter be discussed.

The base 2, the band ring 5 and the sealing ring 8 are, preferably comprised of a soft, resilient material, such as, for example, silicone; and the sleeve 3, cover 4 and valve disc 7 preferably are made of a suitable hard, light weight plastic material, and the spring 9 is preferably made of a suitable corrosion-resistant material, such as, for example, stainless steel or spring steel.

As previously set forth, the sleeve 3 is, preferably, of a one-piece construction and embodies a tubular housing 14 having a spider 15 disposed therein, FIGS. 13–15, the spider 15 having a post 16 projecting outwardly therefrom through one end 3a of the sleeve 3 along the longitudinal center line of the latter, FIGS. 13–15. The tubular housing 14 of the sleeve 3 has an annular groove 18 formed in and extending around the outer surface thereof, with a plurality of holes or openings 20 extending radially through the wall of the housing 14, within the annular groove 18, the opening or openings 20 being disposed in a plane parallel to the spider 15 in surrounding relation to the post 16, FIGS. 13–15. In the valve assembly 1, the band ring 5 is mounted in the annular groove 18 in snug fitting, overlying relation to the opening or openings 20.

In the completed valve assembly 1, the base 2 is mounted on the end portion 3b of the sleeve 3 remote from the post 13 with a snug, but freely removable fit. Preferably, the sleeve 3 has a flange 21 on the end 3b adjacent to the base 2 on the sleeve 3. At the other end 3a of the sleeve 3, the cover 4 is mounted on the sleeve 3 with a snug, but freely removable fit, in outwardly spaced relation to the band ring 5, FIGS. 13–15. The outer end of the cover 4 is in the form of a spider 24, FIG. 4, which has an opening 22 through the center thereof, through which the post 16 extends in the assembled valve 1 and a plurality of openings 23 therein which permits air to be inhaled into the valve assembly, as will be described.

The disc 7 is round and flat in shape, and is of smaller diameter than the sleeve 3. The disc 7 has an opening 7a through the center thereof, FIG. 4. In the assembled valve 1, the disc 7 is mounted on the post 16 with a snug, but freely slidable fit, the post 16 extending through the opening 7a (FIGS. 13–15). The disc 7 has a correspondingly shaped sealing ring or washer 8, made of a suitable soft, resilient material associated therewith, the sealing ring 8 having an opening 8a through the central portion thereof and being slidably mounted on the post 16 in covering relation to the disc 7 on the opposite side thereof from the spider 15.

The spiral spring 9 is mounted on the post 16 in surrounding relation thereto, between the sealing ring 8 and the central portion of the spider 24 in the cover 4. The cover 4 has an inwardly projecting, annular valve seat 28 embodied therein in surrounding relation to the spider 24. The valve seat 22 is smaller in diameter than the disc 7.

In the operation of the valve assembly 1, during normal vegetative breathing, the spring 9 is effective to bias the disc 7 against, or closely adjacent to the spider 15 in the housing 3, the position as shown in FIG. 13. In this open position of the disc 7, air may freely flow around the disc 7 into and out of the valve assembly 1. When a person wearing the valve assembly 1 wishes to speak, the person's increased respiratory effort, for example, airflow, pressure or the like, from the person's lungs or trachea 26 is effective to move the disc 7 away from the spider 15, against the urging of the spring 9 and into position to press the sealing ring 8 into sealing engagement with the valve seat 28, the position as shown in FIG. 14. Thus, sealed, the valve assembly diverts the exhaled air through a fenestrated tube or a tracheoesophageal puncture voice prosthesis device enabling speech. When the person stops speaking, the attendent increased air pressure within the valve assembly 1 decreases and the spring 9 is again effective to bias the disc 7 and the sealing ring 8 back toward the spider 15, out of sealing engagement with the valve seat 28 and thereby permit the exhalation and flow of air through the valve assembly 1 to resume, the position as shown in FIG. 13. However, when large pressures are generated within the valve assembly 1, such as, for example, when a person wearing the same coughs, or the like, this buildup of air pressure is effective to move the disc 7 and sealing ring 8 against the urging of the spring 9 into sealing engagement with the valve seat 28 to seal the assembly. Under such circumstances, if the closing of the disc 7 against the valve seat 28 was permitted to continue to prevent the flow of air outwardly from the trachea 26 of the person wearing the valve assembly 1, the person would be in distress. However, with the novel valve assembly 1, when a large air pressure buildup occurs, thus closing the disc 7 against the valve seat 28, the increased air pressure within valve assembly is effective to cause the elastic ring 5 to be displaced outwardly away from the sleeve 3, the position as shown in FIG. 15. The air pressure exerted outwardly through the openings 20 is effective to displace the ring 5 and to permit the air to flow outwardly through the opening or openings 20 past the ring 5. This particular structure provides a separate external blow-out or relief valve means which automatically closes to restore itself when the air pressure within the valve is reduced, a result which has been unattainable by the prior art structures.

It will be seen that, with the present invention, the valve assembly 1 effectively accommodates breathing during various types of activities, ranging from physical exercise, normal vegetative breathing, speaking, and coughing. Also, as will be appreciated by those skilled in the art, with the construction of the described novel valve assembly 1, springs 9 of different strengths may be predeterminedly selected and used to accommodate the unlimited breathing requirements of various individuals and the separate blow-out valve means may be predeterminely tuned to displace the resilient ring 5 therefrom at a pressure which is more sensitive to a sudden pulse of pressure within the valve assembly. Also, the blow-out valve means automatically closes when the air pressure within the assembly is reduced, which eliminates the need for removal or manual refitting of the prior art tracheostoma valve assemblies.

In addition, the construction of valve assembly 1 is such that if desired, it may be quickly and easily disassembled and reassembled for purposes of cleaning the same and it will be seen that with the construction of the novel valve assembly 1, various parts, such as the base 2, band ring 5, disc 7, sealing ring 8, or spring 9, may be quickly and easily individually replaced if they should become worn or damaged so that repairs may be readily and economically made to such a damaged or worn valve without the necessity of replacing the entire unit.

Thus, in accordance with the present invention, the differential sensitivity of either the relief valve and the internal valve may be differentially tuned or adjusted, either independently or together, to permit the user of the present invention to accommodate a variety of respiratory requirements. Such accommodation on a reliable and consistant basis is simply not achieved by the prior art tracheostoma valves and the present invention will not experience changes in their operating condition over time, as are true of the prior art structures.

In addition, it will be seen that the present invention affords a novel tracheastoma valve which is practical, efficient and reliable in operation and which may be readily and economically produced commercially.

Thus, while we have illustrated and described the preferred embodiments of the present invention, it is to be understood that this is capable of variation and modification, and we, therefore, do not wish to be limited to the precise details set forth but desire to avail ourselves of such changes and alterations as fall within the purview of the following claims.

We claim:

1. A tracheostoma valve assembly comprising:
   a tubular body portion having at least one opening through the side wall thereof and an abutment member mounted therein;
   a sealing ring adapted to engage one end of said tubular body portion;
   a resilient band ring mounted on said body portion in overlying relation to said at least one opening in position to normally close the latter against air flow therethrough, said ring being displaceable outwardly away from said body portion to thereby permit outward flow of air outwardly through said at least one opening when the air pressure in said body portion is above a predetermined pressure,
   a cover member having fluid passageway means therein adapted to mount to said one end of said body portion to hold said sealing ring to said body portion;
   a valve disc, having an outside diameter less than the inside diameter of said body portion and having at least one opening therein, mounted in said body portion for movement back and forth longitudinally thereof between said sealing ring and said abutment member,
   flexible valve means mounted in said body portion between said disc and said abutment means, with said flexible valve means pivotally moving away from said openings in said disc to an open position to permit airflow into the valve assembly during breathing inhalation and pivotally moving to engage said disc and said at least one opening therein to a closed position to seal the same during breathing exhalation, spring means for biasing said disc away from said sealing ring and toward said abutment member, said spring means being of such predetermined strength such as to bias said disc away from said sealing ring and toward said abutment member during non-speech breathing exhalation through said valve and to permit said disc to move to engage said sealing ring during an increased respiratory effort within said tubular body, and wherein said resilient band ring is disposed in closing relation to said at least one opening during vegetative breathing and said increased pressure during speech through said valve, with said resilient ring being disposed in outwardly displaced position relative to at least one opening when the air pressure in said body portion is above a predetermined pressure.

2. A tracheostoma valve in accordance with claim 1, wherein said at least one opening in said tubular body portion comprises spaced openings extending radially through the side wall of said body portion.

3. The tracheostoma valve in accordance with claim 1, wherein said abutment member comprises a spider having dependent legs engageable with the side walls of said body portion.

4. The tracheostoma valve in accordance with claim 1, wherein said spring means is a spiral spring positioned between said cover member and said valve disc to bias said disc away from said sealing ring.

5. The tracheostoma valve in accordance with claim 3, wherein said abutment member is axially mounted within said tubular body portion substantially about the longitudinal midpoint and said dependent legs engage with said side walls of said body portion adjacent the end of said body portion opposite said one end of said body portion.

6. The tracheostoma valve in accordance with claim 1, wherein said at least one opening in said valve disc comprises three openings spaced therein.

7. A tracheostoma valve, including in combination:
 a. a tubular body portion comprising
  (1) a tubular center body portion,
  (2) an attachment flange on one end of said center body portion for attaching said valve to a person or to a tracheostomy tube, and
  (3) a sealing ring adapted to engage the end of said center body portion opposite said one end,
  (4) a cover member having fluid passageway means therein adapted to be mounted on said end of said center body portion, opposite said one end and retaining said sealing ring to said tubular body portion,
 b. said center body portion having
  (1) an abutment therein,
  (2) a post projecting from said abutment and extending along the longitudinal center line of said body portion through said cover member,
  (3) air passage means extending through the sidewall of said body portion,
 c. said cover member having an opening extending therethrough,
 d. a valve disc movably mounted on said post for movement therealong, between a closed position wherein said disc engages said sealing ring and an open position wherein said disc engages said abutment,
 e. said valve disc
  (1) being disposed in covering relation to said opening, to thereby prevent the flow of air through said cover, when said disc is disposed in said engagement with said sealing ring in the closed position, and
  (2) being smaller in diameter than said center body portion to permit the flow of air through said opening when disposed in said open position, and
  (3) having at least one opening therein
 f. a flexible valve member mounted on said post between said abutment and said disc for pivotal movement away from said at least one opening in said disc to permit the flow of air through said at least one opening when the person is inhaling and for pivotal movement towards said disc and said at least one opening to seal the same during exhalation,
 g. a spring disposed and positioned between said cover, said spring being effective to bias said disc away from said sealing ring and toward said abutment to said open position,
 h. said spring
  (1) being operable to bias said disc to said open position from said sealing ring during non-speech breathing exhalation through said tubular body portion, and
  (2) being operable to permit said disc to move to said closed position in sealing engagement with said sealing ring during an increased respiratory effort through said tubular body portion,
 i. a stretchable ring mounted on said center body portion and positioned to normally be disposed in covering, closing relation to said air passage means,
 j. said ring being of such resilient predetermined strength as to
  (1) remain in said closing relation to said remain in said closing relation to said air passage means and thereby prevent flow of air therethrough when the airflow within said tubular body portion is substantially equal to said increased respiratory effort, and
  (2) be displaced outwardly by air pressure and thereby permit the flow of air outwardly through said air passage means when said air pressure within said body portion is substantially greater than said increased respiratory effort.

8. A tracheostoma valve in accordance with claim 7, wherein said air passage means comprise spaced openings extending through the side wall of said center body portion.

9. A tracheostoma valve in accordance with claim 7, wherein said spring means comprises a spiral spring disposed around said post in abutting engagement with said cover member and said disc.

10. A tracheostoma valve in accordance with claim 7, wherein said center body portion is substantially cylindrical in shape, said abutment comprises a spider, said cover member comprises a spider and said disc comprises a substantially flat round member having a diameter less than the internal diameter of said center body portion.

11. A tracheostoma valve in accordance with claim 7, wherein said attachment flange, said cover member and said ring are removably mounted on said center body portion.

12. A tracheostoma valve in accordance with claim 7, wherein said attachment flange, said cover member and said ring are removably mounted on said center body portion with a slidable friction fit.

13. A tracheostoma valve, including in combination:
a. a tubular body portion comprising
   (1) a tubular center body portion,
   (2) an attachment flange on one end of said center body portion for attaching said valve to a person, and
   (3) a cover member having fluid pressure means therein mounted on the other end of said center body portion,
b. said center body portion having
   (1) an abutment therein,
   (2) a post projecting from said abutment and extending along the longitudinal center line of said center body portion through said cover member, and
   (3) air passageway means extending through the side wall of said body portion,
c. said cover member having
   (1) an opening extending therethrough, and
   (2) a valve seat extending around said opening and projecting toward said abutment,
d. a disc movably mounted on said post for movement therealong, back and forth between engagement with said valve seat and with said abutment,
e. said disc
   (1) having a sealing ring associated therewith for engagement with said valve seat,
   (2) being disposed in cover relation to said opening, to thereby prevent the flow of air through said cover, when said disc and said sealing ring is disposed in said engagement with said valve seat, and
   (2) being smaller in width than said center body portion and ineffective to prevent the flow of air through said opening when disposed out of said sealing engagement with said valve seat,
f. a spring disposed in position between said cover and said disc effective to yieldingly urge said disc and said sealing ring away from said valve seat and toward said abutment,
g. said spring
   (1) being operable to hold said disc in spaced relation to said valve seat during non-speech breathing exhalation through said tubular body portion, and
   (2) being inoperable to hold said disc out of said sealing engagement with said valve seat during increased respiratory effort through said tubular body portion,
h. a stretchable ring mounted on said center body portion in position to normally be disposed in covering, closing relation to said air passage means,
i. said ring being of such resilient predetermined strength as to
   (1) remain in said closing relation to said air passage means and thereby prevent flow of air therethrough when the air flow into said tubular body portion is non-speech breathing or increased respiratory effort,
   (2) be displaced outwardly by air pressure and thereby permit the flow of air outwardly through said air passage means when said air pessure within said body portion reaches a predetermined air pressure, and
   (3) return to the closed position when said aire pressure falls below a predetermined air pressure.

14. A tracheostoma valve in accordance with claim 13, wherein said air passage means comprise spaced openings extending through the side wall of said center body portion.

15. A tracheostoma valve in accordance with claim 13, wherein said spring means comprises a spiral spring disposed around said post in abutting engagement with said cover member and said disc.

16. A tracheostoma valve in accordance with claim 13, wherein said center body portion is substantially cylindrical in shape, said abutment comprises a spider, said cover member comprises a spider valve seat, said valve seat and said disc comprises a substantially flat round member, having a diameter greater than that of said valve seat, and less than the internal diameter of said center body portion.

17. A tracheostoma valve in accordance with claim 13, wherein said attachment flange, said cover member and said ring are removably mounted on said center body portion.

18. A tracheostoma valve in accordance with claim 13, wherein said attachment flange, said cover member and said ring are removably mounted on said center body portion with a slidable friction fit.

19. A tracheostoma valve comprising:
a tubular body portion having at least one opening through the side wall thereof and having an annular valve seat positioned therein and abutment member spaced from each other therein;
an external relief valve means including a resilient ring mounted on said body portion in overlying relation to said at least one opening and positioned to normally close the latter against airflow therethrough, said resilient ring being displaceable outwardly away from said body portion to thereby permit outward flow of air through said at least one opening when the air pressure in said body portion is above a predetermined pressure, and
an internal valve means positioned within said tubular body portion, said internal valve means including a valve disc, having an outside diameter less than the inside diameter of said tubular body portion, mounted in said body portion for movement longitudinally thereof between said valve seat and said abutment member between a closed and an open position, respectively, and spring means for yieldingly urging said disc away from said valve seat and toward said abutment member and said open position, with said spring means being of such predetermined strength as to bias said disc away from said valve seat to said open position during non-speech breathing exhalation through said valve and to permit said disc to move and to engage with said valve seat in said closed position as a result of an increased respiratory effort through said internal valve means, with said external relief valve means and said resilient ring thereon being disposed in closing relation to said at least one opening during said vegetative breathing and said increased respiratory effort through said valve, with said resilient ring being disposed in outwardly displaced position relative to at least one opening when the air pressure in said body portion is above a predetermined pressure.

20. The tracheostoma valve assembly in accordance with claim 19, wherein said valve disc includes a plurality of openings therein and said internal valve means further includes a flexible valve member mounted in said body portion for pivotal movement between said abutment member and said disc with said flexible valve moving away from said disc and said openings therein to permit the flow of air into the valve assembly during vegetative breathing inhalation and pivotally moving towards said disc and said opening therein to seal the same during vegetative breathing exhalation.

* * * * *

UNITED STATES PATENT AND TRADEMARK OFFICE
CERTIFICATE OF CORRECTION

PATENT NO. : 4,582,058
DATED      : April 15, 1986
INVENTOR(S) : Depel, Weinberg & Moon It is certified that error appears in the above-identified patent and that said Letters Patent is hereby corrected as shown below:

Column 1, line 42 "thier" should be --their--;

Column 12, lines 39 & 40 after "said" delete "remain in said closing relation to said", this phrase is printed twice;

Column 13, line 11, after fluid delete "pressure", and insert --passageway--;

Column 13, line 37, change "(2)" to --(3)--;

Column 14, line 1, "aire" should be --air--.

Signed and Sealed this

Thirtieth Day of September 1986

[SEAL]

Attest:

Attesting Officer

DONALD J. QUIGG

Commissioner of Patents and Trademarks